(12) United States Patent
Abraham et al.

(10) Patent No.: US 9,289,520 B2
(45) Date of Patent: Mar. 22, 2016

(54) METHOD AND SYSTEM TO CLEAN MICROORGANISMS WITHOUT CHEMICALS

(71) Applicant: Kimberly-Clark Worldwide, Inc., Neenah, WI (US)

(72) Inventors: Jose K. Abraham, Neenah, WI (US); Paige Anunson, Larsen, WI (US); Kathleen C. Engelbrecht, Kaukauna, WI (US); David W. Koenig, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 80 days.

(21) Appl. No.: 14/191,617

(22) Filed: Feb. 27, 2014

(65) Prior Publication Data

US 2015/0238642 A1    Aug. 27, 2015

(51) Int. Cl.
*A61L 2/00* (2006.01)
*A62B 7/08* (2006.01)
*B01J 19/08* (2006.01)
*A61L 2/03* (2006.01)

(52) U.S. Cl.
CPC .......................................... *A61L 2/03* (2013.01)

(58) Field of Classification Search
CPC ............................................................. A61L 2/00
USPC .................... 422/4, 22, 121, 186.04, 186.05
See application file for complete search history.

(56) References Cited

U.S. PATENT DOCUMENTS

| | | |
|---|---|---|
| 2,980,933 A | 4/1961 | Schwartz et al. |
| 3,556,932 A | 1/1971 | Coscia et al. |
| 3,556,933 A | 1/1971 | Williams et al. |
| 3,585,104 A | 6/1971 | Kleinert |
| 3,700,623 A | 10/1972 | Keim |

(Continued)

FOREIGN PATENT DOCUMENTS

| | | |
|---|---|---|
| EP | 0 578 365 A1 | 1/1994 |
| GB | 1 360 202 | 7/1974 |

(Continued)

OTHER PUBLICATIONS

Machine Translation of KR200390850, Jul. 28, 2005, 7 pages.

(Continued)

*Primary Examiner* — Monzer R Chorbaji
(74) *Attorney, Agent, or Firm* — Dority & Manning, P.A.

(57) ABSTRACT

A system for removing microorganisms from a surface is described. The system includes a conducting member, a voltage source, and an electrostatic field controller. The conducting member includes a nonwoven material incorporating conductive fibers. The controller is electrically connected to the conducting member and is configured to apply a DC voltage of about 15 volts or less to the conducting member via the voltage source. The surface to be contacted can include any surface present in households, food industry facilities, medical facilities, etc. Such surfaces can include tables, countertops, walls, cabinets, doors, door handles, door knobs, etc. The system can also be used to treat devices used in the aforementioned environments, such as food preparation equipment, medical devices, household appliances, etc. The system can reduce the amount of microorganisms on the surface by at least about 1 log (90%) without the use of chemicals, high voltages, or long exposure times.

20 Claims, 4 Drawing Sheets

(56) References Cited

U.S. PATENT DOCUMENTS

| | | |
|---|---|---|
| 3,772,076 A | 11/1973 | Keim |
| 3,855,158 A | 12/1974 | Petrovich et al. |
| 3,899,388 A | 8/1975 | Petrovich et al. |
| 4,129,528 A | 12/1978 | Petrovich et al. |
| 4,147,586 A | 4/1979 | Petrovich et al. |
| 4,222,921 A | 9/1980 | Van Eenam |
| 4,375,401 A | 3/1983 | Catsimpoolas |
| 4,594,130 A | 6/1986 | Chang et al. |
| 4,793,898 A | 12/1988 | Laamanen et al. |
| 5,173,164 A | 12/1992 | Egen et al. |
| 5,429,686 A | 7/1995 | Chiu et al. |
| 5,578,460 A | 11/1996 | Ebersole et al. |
| 5,595,628 A | 1/1997 | Gordon et al. |
| 5,656,132 A | 8/1997 | Farrington, Jr. et al. |
| 5,672,248 A | 9/1997 | Wendt et al. |
| 6,096,169 A | 8/2000 | Hermans et al. |
| 6,120,642 A | 9/2000 | Lindsay et al. |
| 6,143,135 A | 11/2000 | Hada et al. |
| 6,197,154 B1 | 3/2001 | Chen et al. |
| 6,224,714 B1 | 5/2001 | Schroeder et al. |
| 6,274,667 B1 | 8/2001 | Shannon et al. |
| 6,287,418 B1 | 9/2001 | Schroeder et al. |
| 6,365,667 B1 | 4/2002 | Shannon et al. |
| 7,687,239 B2 | 3/2010 | Goldberg et al. |
| 8,006,340 B2 | 8/2011 | Ikenaga et al. |
| 8,172,982 B2 | 5/2012 | Ales et al. |
| 8,418,299 B2 | 4/2013 | Thayer et al. |
| 2002/0195331 A1 | 12/2002 | Pitts, Jr. |
| 2009/0114218 A1* | 5/2009 | Veatch .................... 128/202.25 |
| 2012/0196251 A1 | 8/2012 | Taft et al. |
| 2013/0064726 A1 | 3/2013 | Morfill et al. |
| 2013/0276417 A1 | 10/2013 | Winters et al. |

FOREIGN PATENT DOCUMENTS

| | | |
|---|---|---|
| WO | WO 2012177807 A1 | 12/2012 |
| WO | WO 2013159107 A1 | 10/2013 |

OTHER PUBLICATIONS

International Search Report and Written Opinion for PCT/IB2015/050283 dated May 27, 2015, 11 pages.
Machine Transaltion of Japanese Patent—JPH11156991 A2, Jun. 15, 1999, 8 pages.
Machine Translation of Japanese Patent—JP2003001263 A2, Jan. 7, 2003, 13 pages.

* cited by examiner

METHOD AND SYSTEM TO CLEAN MICROORGANISMS WITHOUT CHEMICALS

BACKGROUND

The presence of microorganisms such as bacteria, viruses, and fungi on surfaces with which the general population comes into contact every day can put the population at risk for developing numerous illnesses and diseases. For instance, these microorganisms can be present on surfaces in hospitals, nursing homes, schools, restaurants, grocery stores, kitchens, bathrooms, gyms, etc. One approach to clean these surfaces is to kill and/or remove the microorganisms via the use of sprays or solutions containing detergents, biocides, antibiotics, or other chemicals. However, although the detergents, biocides, antibiotics, or other chemicals used can be successful in killing or removing the microorganisms from the surface, exposure to these chemicals can be harmful. Further, these chemicals may not be "green" and could pose a threat to the environment. Moreover, increased use of such chemicals can lead to the microorganisms having increased resistance to detergents, biocides, antibiotics, and other chemicals. Additionally, over time, the use of such chemicals can corrode or damages the surfaces to which they are applied.

To alleviate the aforementioned problems with using chemicals for the removal of microorganisms, another approach has been to attempt to remove the microorganisms without the use of chemicals, such as by ionization or the use of electric currents. However, these approaches require that a high voltage of from about 5 kilovolts to about 25 kilovolts be applied and/or that the voltage be applied for a long time period, such as up to about 24 hours. Such high voltage can be dangerous in a consumer setting for household use, and requiring application of the voltage over such a long time period is not an effective or efficient method of removing microorganisms from a surface.

In light of the above, a need exists for a system and method of removing microorganisms from a surface without the use of antibiotics, biocides, or other chemical treatments and without the application of high voltages for extended periods of time.

SUMMARY

Aspects and advantages of the present disclosure will be set forth in part in the following description, or may be obvious from the description, or may be learned through practice of the invention.

One exemplary aspect of the present disclosure is directed to a system for removing microorganisms from a surface. The system includes a conducting member, a voltage source, and an electrostatic field controller. The conducting member includes a nonwoven material, wherein the nonwoven material includes conductive fibers (e.g., conductive hollow fibers), conducting sheets, etc. The electrostatic field controller is electrically connected to the conducting member, wherein the controller is configured to apply a direct current voltage of about 15 volts or less to the conducting member via the voltage source.

Another exemplary aspect of the present disclosure is directed to a method for removing microorganisms form a surface. The method includes contacting the surface with a conducting member that includes a nonwoven material, wherein the nonwoven material includes conductive fibers; applying a direct current voltage of about 15 volts or less to the conducting member using an electrostatic field controller coupled to a voltage source; and maintaining contact between the surface and the conducting member, wherein the microorganisms are transferred from the surface to the conducting member.

These and other features, aspects and advantages of the present disclosure will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present disclosure, including the best mode thereof to one skilled in the art, is set forth more particularly in the remainder of the specification, including reference to the accompanying figures, in which.

Figure 1:
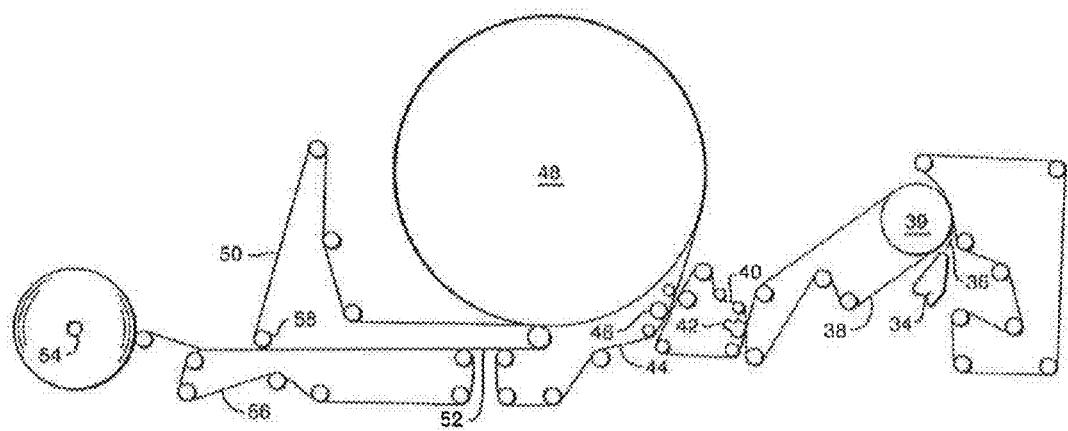
FIG. 1 is a side view of one embodiment of a process of forming a conductive nonwoven material used in the system and method of the present disclosure.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

Generally speaking, the present disclosure is directed to a method and system for removing microorganisms from a surface. For instance, the system can be used to remove microorganisms such as bacteria, viruses, and fungi from any surface to which such microorganisms can attach, including any surfaces present in households, medical facilities, food industry facilities, etc. Such surfaces can include tables, countertops, walls, cabinets, doors, door handles, door knobs, etc. The system can also be used to treat any devices used in the aforementioned environments, such as food preparation equipment, medical equipment and devices, household appliances, etc.

In one embodiment, for instance, the system can include a conducting member comprising a nonwoven material, a voltage source, and an electrostatic field controller electrically connected to the first conducting member. Further, the controller can include one or more control devices, such as a microcontroller, a microprocessor, an integrated circuit logic device, or any other control device. The controller is configured to provide a direct current voltage of about 15 volts or less to the conducting member via the voltage source. In another embodiment, a method for removing microorganisms from a surface is also contemplated. The method includes contacting the surface with a conducting member comprising a nonwoven material, wherein the nonwoven material comprises conductive fibers; applying a direct current voltage of about 15 volts or less, such as from about 1 volt to about 15 volts, such as from about 2 volts to about 12 volts, such as from about 3 volts to about 10 volts, to the conducting member using an electrostatic field controller coupled to a voltage source; and maintaining contact between the surface and the conducting member, wherein the microorganisms are transferred from the surface to the nonwoven material. The nonwoven material can be applied with a positive voltage to attract negatively charged microorganisms to the nonwoven material, thus removing such microorganisms from the contacted surface. Without intending to be limited by theory, it is believed that the negatively charged microorganisms become attracted to the positively charged conducting member such that the microorganisms are transferred from the contacted surface to the conducting member, where they become trapped in the interspace between fibers that form the nonwoven material due to electrophoretic attraction and a capillary force mechanism. The system and method can reduce the amount of microorganisms on the surface, such as by at least about 1 log (90%), without the use of chemicals, high voltages such as those in the kilovolt range, or long exposure times.

The conducting member, which can be used as a trap for microorganisms present on a surface to be cleaned, includes a nonwoven material that can contain conductive fibers (e.g., hollow conductive fibers), conducting sheets, etc., as is discussed in more detail below. The conducting member in the form of a nonwoven material can be electrically connected to an electrostatic field controller that can provide power from a voltage source, such as a battery, to render the conducting member electrically conductive. The controller and voltage source can be arranged in a housing, and the conducting member can be removably attached to an outer surface of the housing. A surface to be treated can then be contacted with the outer surface of the housing to which the conducting member is attached, and the controller can be activated so that a voltage is applied to the conducting member for a sufficient amount of time for microorganisms present on the surface to transfer from the surface to the conducting member via electrophoretic attraction. For instance, a direct current voltage of about 15 volts or less, such as from about 1 volt to about 15 volts, such as from about 2 volts to about 12 volts, such as from about 3 volts to about 10 volts can be applied to the conducting member, and the conducting member can be in contact with the surface to be treated for about 30 minutes or less, such as from about 1 minute to about 30 minutes, such as from about 2 minutes to about 20 minutes, such as from about 3 minutes to about 15 minutes.

The conductive fibers can be incorporated into the nonwoven material, for instance, such that the nonwoven material is electrically conductive. The nonwoven material can also include pulp fibers and can be made using a paper making process. For instance, in one embodiment, the conductive fibers can be combined with pulp fibers and water to form an aqueous suspension of fibers that is then deposited onto a porous surface for forming a conductive nonwoven material. The conductivity of the resulting nonwoven material can be controlled by selecting particular conductive fibers, locating the fibers at particular locations within the nonwoven material and by controlling various other factors and variables. In one embodiment, for instance, the conductive fibers incorporated into the nonwoven material can include chopped carbon fibers.

The conducting member used in the present disclosure can be made by combining conductive fibers with pulp fibers or any other suitable fibers to form a nonwoven material. In one embodiment, the conductive nonwoven material can be disposable and have a one-time use. As such, the conductive nonwoven material is designed to be attached and detached to an outer surface of the housing in which the electrostatic field controller and voltage source are contained.

The conductive fibers that may be used in the nonwoven material of the system according to exemplary aspects of the present disclosure can vary. Conductive fibers that can be used to form the nonwoven materials include carbon fibers, metallic fibers, conductive polymeric fibers including fibers made from conductive polymers or polymeric fibers containing a conductive material, metal coated fibers, and combinations thereof. Metallic fibers that may be used include, for instance, copper fibers, aluminum fibers, and the like. Polymeric fibers containing a conductive material include thermoplastic fibers coated with a conductive material or thermoplastic fibers impregnated or blended with a conductive material. For instance, in one embodiment, thermoplastic fibers may be used that are coated with silver.

The conductive fibers incorporated into the nonwoven material can have any suitable length and diameter. In one embodiment, for instance, the conductive fibers can have an aspect ratio of from about 100:1 to about 1,000:1.

The amount of conductive fibers contained in the nonwoven material can vary based on many different factors, such as the type of conductive fiber incorporated into the material. The conductive fibers may be incorporated into the nonwoven material, for instance, in an amount from about 1 wt. % to about 90 wt. %, or even greater, based on the total weight of the nonwoven material. In one embodiment, the conductive fibers can be present in the nonwoven material in an amount of from about 2 wt. % to about 20 wt. %, such as from about 5 wt. % to about 15 wt. %, such as from about 8 wt. % by weight to about 12 wt % based on the total weight of the nonwoven material.

Carbon fibers that may be used in the present disclosure include fibers made entirely from carbon or fibers containing carbon in amounts sufficient so that the fibers are electrically conductive. In one embodiment, for instance, carbon fibers may be used that are formed from a polyacrylonitrile (or PAN) polymer. In particular, the carbon fibers are formed by heating, oxidizing, and carbonizing polyacrylonitrile PAN polymer fibers. Such fibers typically have high purity and contain relatively high molecular weight molecules. For instance, the fibers can contain carbon in an amount greater than about 85% by weight. In one embodiment, for instance, the purity of the carbon fibers can be from about 85% to about 95%, such as from about 88% to about 92%. Although higher purity fibers have better conductive properties, the higher purity fibers can be more expensive. Sufficient electrical characteristics, on the other hand, can be obtained using fibers with the purity ranges described above.

In order to form carbon fibers from polyacrylonitrile PAN polymer fibers, the polyacrylonitrile PAN fibers are first heated in an oxygen environment, such as air. While heating, cyano sites within the polyacrylonitrile PAN polymer form repeat cyclic units of tetrahydropyridine. As heating continues, the polymer begins to oxidate. During oxidation, hydrogen is released causing carbon to form aromatic rings.

After oxidation, the fibers are then further heated in an oxygen starved environment. For instance, the fibers can be heated to a temperature of greater than about 1300° C., such as greater than 1400° C., such as from about 1300° C. to about 1800° C. During heating, the fibers undergo carbonization. During carbonization, adjacent polymer chains join together to form a lamellar, basal plane structure of nearly pure carbon.

Polyacrylonitrile-based carbon fibers are available from numerous commercial sources. For instance, such carbon fibers can be obtained from Toho Tenax America, Inc. of Rockwood, Tenn. Other raw materials used to make carbon fibers are Rayon and petroleum pitch.

Of particular advantage, the formed carbon fibers can be chopped to any suitable length. In one embodiment of the present disclosure, for instance, chopped carbon fibers that can be incorporated into the nonwoven material can have a length of from about 1 millimeters (mm) to about 15 mm, such as from about 2 mm to about 10 mm, such as from about 3 mm to about 8 mm. Further, the fibers can have an average diameter of from about 1 micron to about 20 microns, such as from about 3 microns to about 15 microns, such as from about 5 microns to about 10 microns. In one embodiment, for instance, the carbon fibers can have a length of about 3 mm and an average diameter of about 7 microns.

In one embodiment, the carbon fibers incorporated into the nonwoven material can have a water soluble sizing. Sizing can be in the amount of 0.1 wt. % to about 10 wt. %, such as from about 0.5 wt. % to about 8 wt. %, such as from about 1 wt. % to about 5 wt. % based on the weight of the nonwoven material. Water soluble sizings, can be, but not limited to, polyamide compounds, epoxy resin ester and poly(vinyl pyrrolidone). In this manner, the sizing is dissolved when mixing the carbon fibers in water to provide a good dispersion of carbon fibers in water prior to forming the nonwoven material. The sizing also assists in handling the fibers, by controlling them from becoming airborne while being added during the process.

In forming conductive nonwoven materials used in accordance with the present disclosure, the above conductive fibers are combined with other fibers suitable for use in tissue or paper making processes. The fibers combined with the conductive fibers may comprise any natural or synthetic cellulosic fibers including, but not limited to nonwoody fibers, such as cotton, abaca, kenaf, sabai grass, flax, esparto grass, straw, jute hemp, bagasse, milkweed floss fibers, algae fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898 to Laamanen et al.; U.S. Pat. No. 4,594,130 to Chang et at; and U.S. Pat. No. 3,585,104 to Kleinert. Useful fibers can also be produced by anthraquinone pulping, exemplified by U.S. Pat. No. 5,595,628 to Gordon, et al.

In one embodiment, softwood fibers are used to produce the nonwoven material. Softwood fibers tend to be longer which reduces particulate emission during manufacturing and converting. The longer pulp fibers also have a tendency to entangle better with the conductive fibers, such as the carbon fibers.

The pulp fibers incorporated into the nonwoven material, such as softwood fibers, can also be refined so as to increase the amount of bonding sites on each fiber. The increase in bonding sites increases the mechanical entanglement of the pulp fibers with the conductive fibers in the finished material. This allows for a very flat uniform paper with reduced carbon fiber fallout during processing. The refining action also increases the overall strength of the nonwoven material. For example, in one embodiment, the pulp fibers can have a Canadian Standard Freeness of greater than about 350 milliliters, such as greater than about 375 milliliters. For instance, the pulp fibers can be refined so as to have a Canadian Standard Freeness of from about 350 milliliters to about 600 milliliters.

A portion of the fibers, such as up to 50% or less by dry weight, or from about 5% to about 30% by dry weight, can be synthetic fibers such as rayon, polyolefin fibers, polyester fibers, polyvinyl alcohol fibers, bicomponent sheath-core fibers, multi-component binder fibers, and the like. An exemplary polyethylene fiber is PULPEX™, available from Hercules, Inc. (Wilmington, Del.). Synthetic cellulose fiber types include rayon in all its varieties and other fibers derived from viscose or chemically-modified cellulose.

Chemically treated natural cellulosic fibers can also be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. Mercerized fibers, regenerated cellulosic fibers, cellulose produced by microbes, rayon, and other cellulosic material or cellulosic derivatives can be used. Suitable fibers can also include recycled fibers, virgin fibers, or mixtures thereof.

Other papermaking fibers that can be used in the nonwoven material of the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a tissue or paper web can be utilized in forming the nonwoven material used in the conducting member of the present disclosure. For example, a papermaking process can utilize embossing, wet pressing, air pressing, through-air drying, uncreped through-air drying, hydroentangling, air laying, as well as other steps known in the art. The nonwoven material may be formed from a fiber furnish containing pulp fibers in an amount of at least 50 wt. %, such as at least 60 wt. %, such as at least 70 wt. %, such as at least 85 wt. %.

Wet and dry strength agents may be applied or incorporated into the nonwoven material used in the system of the present disclosure. As used herein, "wet strength agents" refer to materials used to immobilize the bonds between fibers in the wet state. Typically, the means by which fibers are held together in paper and tissue products involve hydrogen bonds and sometimes combinations of hydrogen bonds and covalent and/or ionic bonds. In the present disclosure, it may be useful to provide a nonwoven material that will allow bonding of fibers in such a way as to immobilize the fiber-to-fiber bond points and make them resistant to disruption in the wet state.

In the present disclosure, wet strength agents also assist in bonding the conductive fibers, such as the carbon fibers, to the rest of the fibers contained in the nonwoven material. In this manner, the conductive fibers are inhibited from falling out of the nonwoven material during further handling and use.

Any material that when added to a nonwoven material or sheet results in providing the tissue sheet with a mean wet geometric tensile strength/dry geometric tensile strength ratio in excess of about 0.1 will, for purposes of the present disclosure, be termed a wet strength agent. Typically these materials are termed either as permanent wet strength agents or as "temporary" wet strength agents. For the purposes of differentiating permanent wet strength agents from temporary wet strength agents, the permanent wet strength agents will be defined as those resins which, when incorporated into paper or tissue products, will provide a paper or tissue product that retains more than 50% of its original wet strength after exposure to water for a period of at least five minutes. Temporary wet strength agents are those which show 50% or less than, of their original wet strength after being saturated with water for five minutes. Both classes of wet strength agents can be used in the nonwoven materials utilized in the system and method according to exemplary aspects of the present disclosure. The amount of wet strength agent added to the pulp fibers may be at least about 0.1 dry weight percent, more specifically about 0.2 dry weight percent or greater, and still more specifically from about 0.1 to about 3 dry weight percent, based on the dry weight of the fibers.

Permanent wet strength agents will typically provide a more or less long-term wet resilience to the structure of a nonwoven material. In contrast, the temporary wet strength agents will typically provide nonwoven materials that had low density and high resilience, but would not provide a structure that had long-term resistance to exposure to water or body fluids.

The temporary wet strength agents may be cationic, non-ionic or anionic. Such compounds include PAREZ™ 631 NC and PAREZ™ 725 temporary wet strength resins that are cationic glyoxylated polyacrylamide available from Cytec Industries (West Paterson, N.J.). These and similar resins are described in U.S. Pat. No, 3,556,932 to Coscia, et al. and U.S. Pat. No. 3,556,933 to Williams, et al. Hercobond 1366, manufactured by Hercules, Inc., located at Wilmington, Del., is another commercially available cationic glyoxylated polyacrylamide that may be used in accordance with exemplary aspects of the present disclosure. Additional examples of temporary wet strength agents include dialdehyde starches such as COBOND™ 1000 from National Starch and Chemical Company and other aldehyde containing polymers such as those described in U.S. Pat. No. 6,224,714 to Schroeder, et al.; U.S. Pat. No. 6,274,667 to Shannon, et al.; U.S. Pat. No. 6,287,418 to Schroeder, et al.; and U.S. Pat. No. 6,365,667 to Shannon et al., the disclosures of which are incorporated by reference herein.

Permanent wet strength agents comprising cationic oligomeric or polymeric resins can be used in the nonwoven material component of the present disclosure. Polyamide-polyamine-epichlorohydrin type resins also referred to as polyaminoamide-epichlorohydrin resins such as KYMENE™ 557H sold by Hercules, Inc., located at Wilmington, Del., are suitable permanent wet-strength agents for use in the nonwoven material in the system and method of the present disclosure. Such materials have been described in U.S. Pat. No. 3,700,623 to Keim; U.S. Pat. No. 3,772,076 to Keim; U.S. Pat. No. 3,855,158 to Petrovich, et al.; U.S. Pat. No. 3,899,388 to Petrovich, et al.; U.S. Pat. No. 4,129,528 to Petrovich et al; U.S. Pat. No. 4,147,586 to Petrovich, et al.; and U.S. Pat. No. 4,222,921 to van Eenam. Other cationic resins include polyethylenimine resins and aminoplast resins obtained by reaction of formaldehyde with melamine or urea. It can be advantageous to use both permanent and temporary wet strength resins in the nonwoven material that is a component of the conducting member of the present disclosure.

In one embodiment, a relatively large amount of a wet strength agent is incorporated into the nonwoven material. The wet strength agent may also add to the dry strength of the product. In addition, wet strength agents aid in the chemical entangling of the fibers in the material to improve the retention of the conductive fibers. The amount of wet strength agent added to the nonwoven material can depend upon various different factors. In general, for instance, the wet strength agent can be added in an amount from about 1 kg/mton to about 12 kg/mton, such as from about 5 kg/mton to about 10 kg/mton. In certain embodiments, it may be desirable to add as much wet strength agent as possible. In these embodiments, for instance, the wet strength agent can be added in amounts greater than about 7 kg/mton, such as in amounts greater than about 8 kg/mton.

Dry strength agents are well known in the art and include but are not limited to modified starches and other polysaccharides such as cationic, amphoteric, and anionic starches and guar and locust bean gums, modified polyacrylamides, carboxymethylcellulose, sugars, polyvinyl alcohol, chitosans, and the like. Such dry strength agents are typically added to a fiber slurry prior to nonwoven material formation or as part of the creping package.

Nonwoven materials made in accordance with the present disclosure can include a single homogeneous layer of fibers or may include a stratified or layered construction. For instance, the nonwoven material ply may include two or three layers of fibers. Regardless of how many layers are contained in the nonwoven material of the system of the present disclosure, in one embodiment, the nonwoven material can generally be made according to a wetlaid process. In this embodiment, the fibers are combined with water to form an aqueous suspension and then deposited onto a porous forming surface where a wet nonwoven material is formed. In one embodiment, an aqueous suspension containing the pulp fibers is first produced. The conductive fibers, such as the carbon fibers, are then injected into the aqueous suspension of pulp fibers prior to depositing the aqueous suspension onto the forming surface. For example, the conductive fibers can be injected into the aqueous suspension of pulp fibers in a headbox just prior to depositing the fibers onto the forming surface. The aqueous suspension of pulp fibers, for instance, may contain greater than 99% by weight water. For instance, in one embodiment, the aqueous suspension of pulp fibers contains the pulp fibers in an amount of less than 1% by weight, such as in an amount of about 0.5% by weight. The conductive fibers can then be injected into the aqueous suspension at a similar dilution. For instance, an aqueous suspension of carbon fibers containing carbon fibers in an amount of about 0.5% by weight may be injected into the aqueous suspension of pulp fibers.

Injecting the conductive fibers into an aqueous suspension of pulp fibers has been found to reduce the formation of flocks of the carbon fibers. It has been discovered that flocks have a greater tendency to form when the amount of time the fibers are mixed together increases. The creation of flocks, for instance, can produce weak spots in the resulting material and cause wet breaks when the nonwoven material is later processed or used in the system and method of the present disclosure.

Once the aqueous suspension of fibers is formed into a nonwoven material, the nonwoven material may be processed using various techniques and methods. For example, referring to FIG. 1, a method is shown for making uncreped, throughdried nonwoven materials. In one embodiment, it may be desirable to form the nonwoven material using an uncreped, through-air drying process. It was found that creping the nonwoven material during formation could cause damage to the conductive fibers by destroying the network of conductive fibers within the nonwoven material, resulting in the nonwoven material becoming non-conductive.

For simplicity, the various tensioning rolls schematically used to define the several fabric runs are shown, but not numbered. It will be appreciated that variations from the apparatus and method illustrated in FIG. 1 can be made without departing from the general process. Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet nonwoven material downstream in the process as the nonwoven material is partially dewatered to a consistency of about 10 dry weight percent. Additional dewatering of the wet nonwoven material can be carried out, such as by vacuum suction, while the nonwoven material is supported by the forming fabric.

The wet nonwoven material is then transferred from the forming fabric to a transfer fabric 40. In one optional embodiment, the transfer fabric can be traveling at a slower speed than the forming fabric in order to impart increased stretch into the nonwoven material. This is commonly referred to as a "rush" transfer. The relative speed difference between the two fabrics can be from about 0% to about 15%, more specifically from about 0% to about 8%. Transfer is preferably carried out with the assistance of a vacuum shoe 42 such that the forming fabric and the transfer fabric simultaneously converge and diverge at the leading edge of the vacuum slot.

The nonwoven material is then transferred from the transfer fabric to the throughdrying fabric 44 with the aid of a vacuum transfer roll 46 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer can be carried out with vacuum assistance to ensure deformation of the sheet to conform to the throughdrying fabric, thus yielding desired bulk and appearance if desired. Suitable throughdrying fabrics are described in U.S. Pat. No. 5,429,686 to Chiu, et al. and U.S. Pat. No. 5,672,248 to Wendt, et al. which are incorporated by reference herein.

In one embodiment, the throughdrying fabric provides a relatively smooth surface. Alternatively, the fabric can contain high and long impression knuckles.

The side of the nonwoven material contacting the throughdrying fabric is typically referred to as the "fabric side" of the nonwoven material. The fabric side of the nonwoven material, as described above, may have a shape that conforms to the surface of the throughdrying fabric after the fabric is dried in the throughdryer. The opposite side of the nonwoven material, on the other hand, is typically referred to as the "air side". The air side of the nonwoven material is typically smoother than the fabric side during normal throughdrying processes.

The level of vacuum used for the nonwoven material transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the nonwoven material to blow the material onto the next fabric in addition to or as a replacement for sucking it onto the next fabric with vacuum. Also, a vacuum roll or rolls can be used to replace the vacuum shoe(s).

While supported by the throughdrying fabric, the nonwoven material is finally dried to a consistency of about 94% or greater by the throughdryer 48 and thereafter transferred to a carrier fabric 50. The dried nonwoven material 52 is transported to the reel 54 using carrier fabric 50 and an optional carrier fabric 56. An optional pressurized turning roll 58 can be used to facilitate transfer of the nonwoven material from carrier fabric 50 to fabric 56. Suitable carrier fabrics for this purpose are Albany International 84M or 94M and Asten 959 or 937, all of which are relatively smooth fabrics having a fine pattern. Although not shown, reel calendaring or subsequent off-line calendaring can be used to improve the smoothness and softness of the nonwoven material. Calendering the nonwoven material may also cause the conductive fibers to orient in a certain plane or in a certain direction. For instance, in one embodiment, the nonwoven material can be calendared in order to cause primarily all of the conductive fibers to lie in the X-Y plane and not in the Z direction. In this manner, the conductivity of the nonwoven material can be improved while also improving the softness of the nonwoven material.

In one embodiment, the nonwoven material 52 is a material which has been dried in a flat state. For instance, the nonwoven material can be formed while it is on a smooth throughdrying fabric. Processes for producing uncreped throughdried fabrics are, for instance, disclosed in U.S. Pat. No. 5,672,248 to Wendt, et al.; U.S. Pat. No. 5,656,132 to Farrington, et al.; U.S. Pat. No. 6,120,642 to Lindsay, et al.; U.S. Pat. No. 6,096,169 to Hermans, et al.; U.S. Pat. No. 6,197,154 to Chen, et al.; and U.S. Pat. No. 6,143,135 to Hada, et al., which are incorporated by reference herein.

In FIG. 1, a process is shown for producing uncreped through-air dried webs or nonwoven materials, it should be understood, however, that any suitable process or technique that does not use creping may be used to form the conductive nonwoven material. For example, referring to FIG. 2, another process that may be used to form the nonwoven materials used in the system and method of the present disclosure is shown. In the embodiment illustrated in FIG. 2, the newly formed nonwoven material is wet pressed during the process.

In this embodiment, a headbox 60 emits an aqueous suspension of fibers onto a forming fabric 62 which is supported and driven by a plurality of guide rolls 64. The headbox 60 may be similar to the headbox 34 shown in FIG. 1. In addition, the aqueous suspension of fibers may contain conductive fibers as described above. A vacuum box 66 is disposed beneath forming fabric 62 and is adapted to remove water from the fiber furnish to assist in forming a nonwoven material. From forming fabric 62, a formed nonwoven material 68 is transferred to a second fabric 70, which may be either a wire or a felt. Fabric 70 is supported for movement around a continuous path by a plurality of guide rolls 72. Also included is a pick up roll 74 designed to facilitate transfer of nonwoven material 68 from fabric 62 to fabric 70.

From fabric 70, nonwoven material 68, in this embodiment, is transferred to the surface of a rotatable heated dryer drum 76, such as a Yankee dryer. As shown, as nonwoven material 68 is carried through a portion of the rotational path of the dryer surface, heat is imparted to the nonwoven material causing most of the moisture contained within the nonwoven material to be evaporated. The nonwoven material 68 is then removed from the dryer drum 76 without creping the nonwoven material.

Release agents that may be used include, for instance, polyamidoamine epichlorohydrin polymers, such as those sold under the trade name REZOSOL™ by the Hercules Chemical Company. Particular release agents that may be used in the present disclosure include Release Agent 247, Rezosol 1095, Crepetrol 874, Rezosol 974, ProSoft TQ-1003 all available from the Hercules Chemical Company, Busperse 2032, Busperse 2098, Busperse 2091, Buckman 699 all available from Buckman Laboratories, and 640C release, 640D release, 64575 release, DVP4V005 release, DVP4V008 release all available from Nalco.

Figure 2:
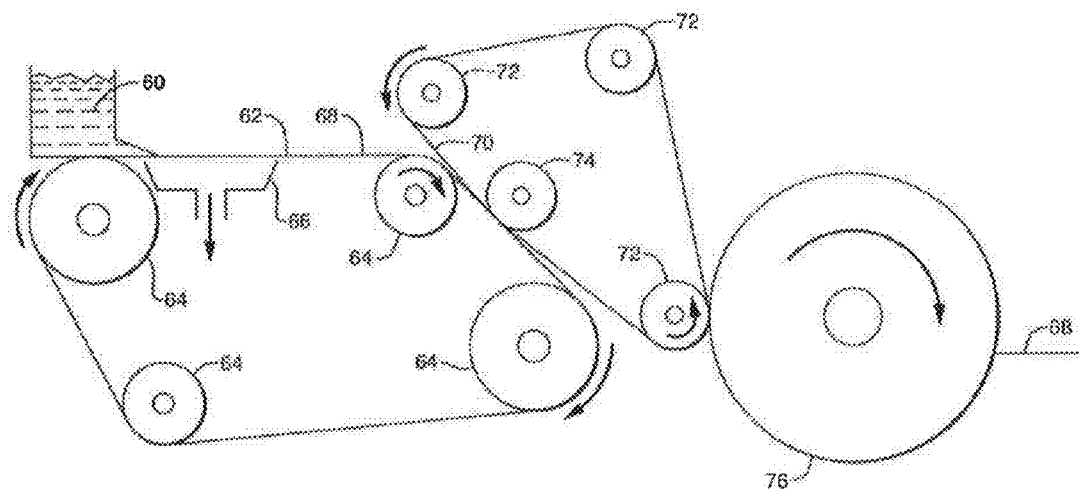
FIG. 2 is a side view of another embodiment of a process for forming a conductive nonwoven material used in the system and method of the present disclosure.

During the process of making the nonwoven material, such as either shown in FIG. 1 or FIG. 2, the nonwoven material can be flattened and densified. One technique for flattening or densifying the material is by feeding the nonwoven material through the nip of opposing calendar rolls. Flattening and densifying the material has been found to reduce fallout of the carbon fiber during further processing. Flattening the nonwoven material also reduces the overall caliper or thickness and increases the electrical conductivity of the material by increasing the conductive fiber network and uniformity. Increased conductivity may allow for an overall reduction in the weight percentage of the conductive fibers contained in the finished nonwoven material.

When calendaring the nonwoven material, the nonwoven material can be calendared in a dry state or in a wet state. In one embodiment, for instance, the calendar rolls may apply a pressure of at least 900 pounds per linear inch (PLI), such as from about 900 PLI to about 1100 PLI. For instance, in one particular embodiment, the pressure applied by the calendaring rolls may be from about 950 PLI to about 1000 PLI, such as a pressure of about 980 PLI.

Nonwoven materials used as the conducting member of the present disclosure can have a basis weight of from about 15 gsm to about 60 gsm or greater. For instance, the nonwoven material can have a basis weight of from about 20 gsm to about 50 gsm, such as from about 30 gsm to about 40 gsm.

Once densified or flattened, the nonwoven material can be made with a relatively low bulk. For instance, as described above, in some processes, the nonwoven material can be densified as it is formed. The bulk of these nonwoven materials, for instance, can be less than about 2 cc/g, such as less than about 1 cc/g, such as less than about 0.5 cc/g.

The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

Nonwoven materials made in accordance with the present disclosure can also have sufficient strength so as to facilitate handling and coming into contact with a wet or dry surface from which microorganisms are to be removed. For instance, in one embodiment, the nonwoven material can have a strength (or peak load) of greater than about 5000 grams force in the machine or length direction, such as greater than about 5500 grams force, such as even greater than about 6000 grams force. Tensile testing of the nonwoven material, for instance, can be conducted on a one inch wide specimen at 300 mm/min and 75 mm gage length.

The conductivity of the nonwoven material can also vary depending upon the type of conductive fibers incorporated into the nonwoven material, the amount of conductive fibers incorporated into the nonwoven material, and the manner in which the conductive fibers are positioned, concentrated or oriented in the nonwoven material. In one embodiment, for instance, the nonwoven material can have a resistance of less than about 1500 Ohms/square, such as less than about 100 Ohms/square, such as less than about 80 Ohms/square. In one embodiment, for instance, the nonwoven material can have a resistance of from about 20 Ohms/square to about 80 Ohms/square, such as from about 20 Ohms/square to about 40 Ohms/square.

The conductivity of the nonwoven material is calculated as the quotient of the resistant measurement of a nonwoven material, expressed in Ohms, divided by the ratio of the length to the width of the nonwoven material. The resulting resistance of the nonwoven material is expressed in Ohms per square. More specifically, the resistance measurement is in accordance with ASTM F1896-98 "Test Method for Determining the Electrical Resistivity of a Printed Conductive Material." The resistance measuring device (or Ohm meter) used for carrying out ASTM F1896-98 is a Fluke multimeter (model 189) equipped with Fluke alligator clips (model AC120); both are available from Fluke Corporation, Everett, Wash.

When using carbon fibers, the resulting nonwoven material is generally gray or black in color. If desired, the material may be dyed a particular shade of color to improve aesthetics. For instance, in one embodiment, the material can be dyed a shade of purple or a shade of blue. Particular dyes that may be used include PANTONE 264U purple dye or PANTONE 291U blue dye.

In an alternative embodiment, the nonwoven material may be laminated using an adhesive or otherwise to other nonwoven or polymeric film materials. For instance, in one embodiment, the nonwoven material may be laminated to a meltblown web and/or a spunbond web that are made from polymeric fibers, such as polypropylene fibers. As described above, in one embodiment, the nonwoven material can contain synthetic fibers. In this embodiment, the nonwoven material may be bonded to an opposing web containing synthetic fibers such as a meltblown web or spunbond web.

Figure 3A:
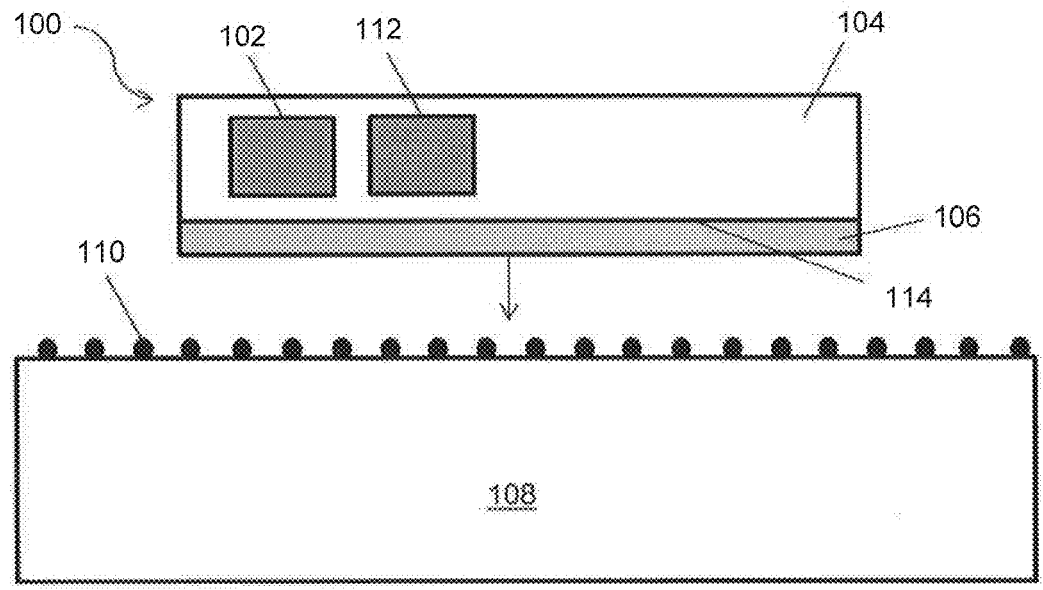
FIG. 3(a) is a cross-sectional side view of a system for removing microorganisms from a surface according to an exemplary embodiment of the present disclosure, prior to coming into contact with the surface.
Figure 3B:
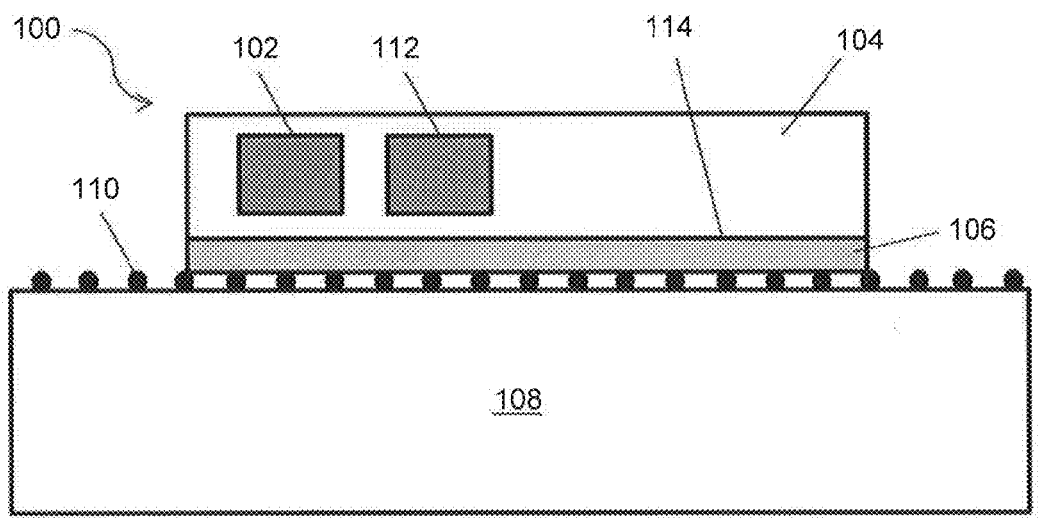
FIG. 3(b) is a cross-sectional side view of a system for removing microorganisms from a surface according to an exemplary embodiment of the present disclosure, while in contact with the surface.
Figure 3C:
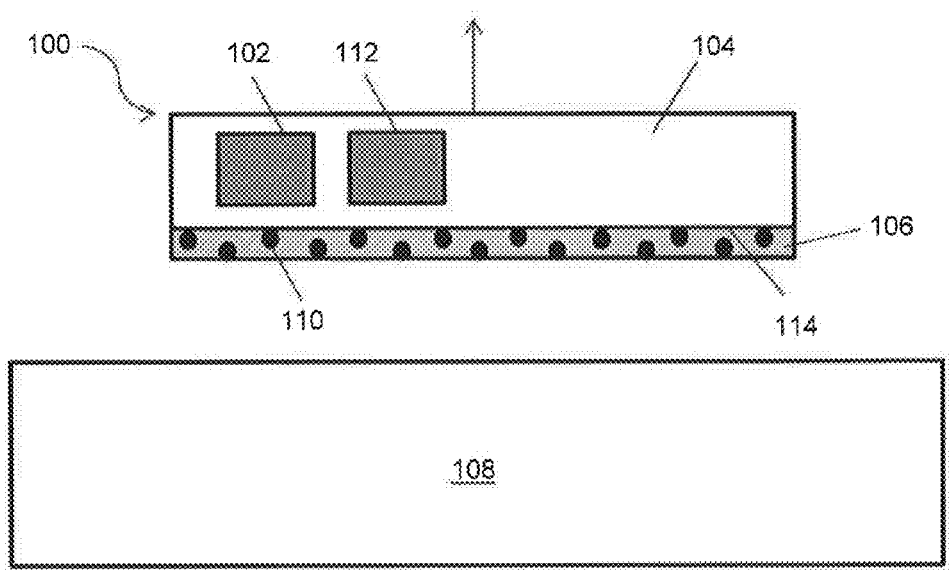
FIG. 3(c) is a cross-sectional side view of a system for removing microorganisms from a surface according to an exemplary embodiment of the present disclosure, after coming into contact with the surface.

Turning now to FIGS. 3(a), 3(b), and 3(c), a method for removing microorganisms from a surface using the system of the present disclosure is described. FIG. 3(a) is a cross-sectional side view of the system for removing microorganisms from a surface, prior to coming into contact with the surface, FIG. 3(b) is a cross-sectional side view of the system for removing microorganisms from the surface while in contact with the surface, and FIG. 3(c) is a cross-sectional side view of the system for removing microorganisms from the surface after coming into contact with the surface. The system 100 includes a housing 104 that contains a voltage source 102 and an electrostatic field controller 112 that regulates the voltage applied from the voltage source 102 to the conducting member 106. The controller 112 can include one or more control devices, such as a microcontroller, a microprocessor, an integrated circuit logic device, or any other control device. The conducting member 106 is attached to an outer surface 114 of the housing 104. During use of the system, the conducting member 106 is contacted with the surface 108 from which microorganisms 110 are to be removed. Then, a direct current voltage of about 15 volts or less, such as from about 1 volt to about 15 volts, such as from about 2 volts to about 12 volts, such as from about 3 volts to about 10 volts can be applied to the conducting member 106 from the voltage source 102 via the controller 112. The contact between the conducting member 106 and the surface 108 to be treated for about 30 minutes or less, such as from about 1 minute to about 30 minutes, such as from about 2 minutes to about 20 minutes, such as from about 3 minutes to about 15 minutes, after which the microorganisms 110 have moved from the surface 108 to the conducting member 106, where they become trapped. The system 100 can reduce the amount of microorganisms 110 on the surface 108 by at least about 1 log (90%), such as by about 2 log (99%), such as by about 3 log (99.9%) without the use of chemicals, kilovolt range voltages, or extended periods of time.

Figure 4:
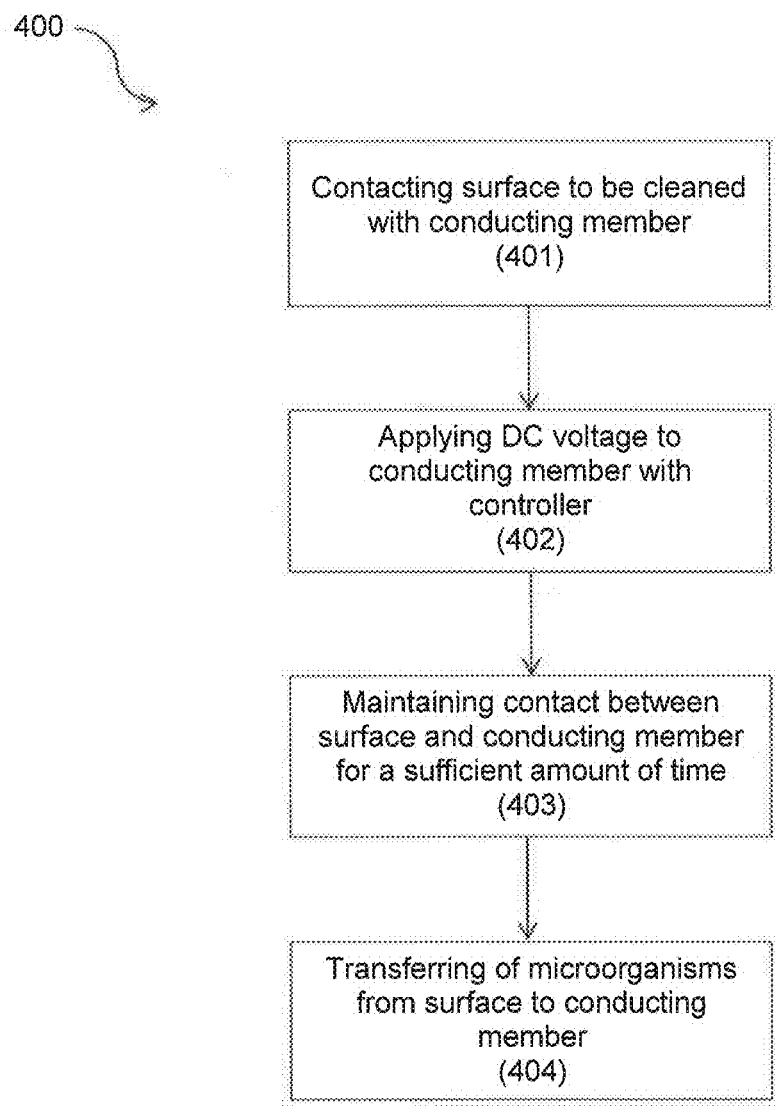
FIG. 4 is a flow chart for a method for removing microorganisms from a surface according to an exemplary embodiment of the present disclosure.

FIG. 4 shows a flow chart demonstrating one method 400 for removing microorganisms from a surface as contemplated by the present disclosure. The method 400 includes contacting the surface to be cleaned with a conducting member (401); applying a DC voltage to the conducting member with a controller (402); maintaining contact between the surface and the conducting member (403); and allowing for a sufficient amount of time to pass to allow for transferring of the microorganisms from the surface to the conducting member (e.g., nonwoven material) 404.

The present disclosure may be better understood by reference to the following examples.

Example 1

Stainless steel coupons were seeded with *Escherichia coli* bacteria under wet and dry conditions and then contacted with the system of the present disclosure. First, *Escherichia coli* ATCC 11229 was cultured in tryptic soy broth (TSB) from Becton Dickinson and Company, Sparks, MD, overnight at 37° C. The cultures were washed once in phosphate buffered saline (PBS) from Thermo Scientific, Waltham, Mass. and diluted 100-fold to about $10^7$ colony forming units/milliliter (CFU/mL) for the dry coupons and diluted 10-fold to about $10^6$ CFU/mL for the wet coupons.

Next, stainless steel coupons were washed and sterilized. The coupons were 2.54 centimeters by 2.54 centimeters and were made from 18 gauge 304 Stainless Steel #8 finish from FedTech, Mounds View, Minn. For the dry samples, 15 microliters of diluted bacteria was inoculated onto the stainless steel coupons, the coupons were allowed to dry for 30 minutes at 37° C. before testing. For the wet samples, 100 microliters of diluted bacteria were stainless steel coupons, and the coupons were tested immediately.

For both the dry and wet testing conditions, nonwoven material containing carbon fibers were placed on to the inoculated side of the stainless steel coupons, and a 40 gram weight was placed on top of the nonwoven material to simulate normal cleaning force. Voltage was then applied to the nonwoven material for one minute using a regulated power supply where current was monitored with a Flueke 189 True-RMS Digital Multimeter available from Fluke Inc., Everest, Mass. Control samples were treated as above but without applying voltage. Then, the bacteria was harvested by shaking at 200 rpm for 3 minutes in 20 millimeters of Letheen broth from Becton Dickinson and Company and then counted.

As shown from Table 1 below, when voltage was applied to the nonwoven material that was in contact with dried bacteria, the bacteria was transferred from the dry stainless steel coupon to the nonwoven material. One log of bacteria (90%) was recovered from the nonwoven material when both 1 volt and 5 volts of voltage were applied. The amount of bacteria present on the nonwoven material increased after voltage was applied compared to when 0 volts were applied.

The nonwoven material was also able to remove and trap bacteria from the wet stainless steel coupons. When 10 volts was applied, there was a reduction of over 1.4 logs of bacteria (>90%) on the stainless steel surface compared to when no voltage was applied.

TABLE 1

| Sample (n = 3) | Voltage Applied (volts) | Log CFU/mL Bacteria Recovered SS Surface | Log CFU/mL Bacteria Recovered Conductive NW | % *E. coli* Moved to NW | % *E. coli* Reduced on SS Surface |
|---|---|---|---|---|---|
| Dry | 0 | 4.42 | 0.00 | N/A | N/A |
|  | 1 | 3.76 | 1.15 | 90 | N/A |
|  | 5 | 3.43 | 1.00 | 90 | N/A |
| Wet | 0 | 3.42 | 4.74 | N/A | N/A |
|  | 10 | <2.0 | 4.27 | N/A | >90 |

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A system for removing microorganisms from a surface comprising:
    a conducting member comprising a nonwoven material, wherein the nonwoven material comprises conductive fibers;
    a voltage source; and
    an electrostatic field controller electrically connected to the conducting member, wherein the controller is configured to apply a direct current voltage of about 15 volts or less to the conducting member via the voltage source.

2. The system of claim 1, wherein the voltage source comprises a battery.

3. The system of claim 1, wherein the voltage source and electrostatic field controller are positioned within a housing.

4. The system of claim 3, wherein the conductive member is attached to an outer surface of the housing.

5. The system of claim 1, wherein the conducting member is disposable.

6. The system of claim 1, wherein the conductive fibers are present in an amount ranging from about 1 wt. % to about 90 wt. %, based on the total weight of the nonwoven material.

7. The system of claim 1, wherein the conductive fibers comprise carbon, copper, aluminum, silver, or a combination thereof, further wherein the conductive fibers are hollow.

8. The system of claim 1, wherein the nonwoven material further comprises cellulosic fibers.

9. The system of claim 1, wherein the system reduces the amount of microorganisms on the surface by at least about 1 log (90%).

10. The system of claim 1, wherein the system reduces the amount of microorganisms on the surface by about 2 log (99%).

11. A method for removing microorganisms from a surface, the method comprising:
   contacting the surface with a conducting member comprising a nonwoven material, wherein the nonwoven material comprises conductive fibers;
   applying a direct current voltage of about 15 volts or less to the conducting member using an electrostatic field controller coupled to a voltage source; and
   maintaining contact between the surface and the conducting member, wherein the microorganisms are transferred from the surface to the conducting member.

12. The method of claim 11, wherein contact is maintained between the surface and the conducting member for a time period of about 30 minutes or less.

13. The method of claim 11, wherein the surface is dry.

14. The method of claim 11, wherein the surface is wet.

15. The method of claim 11, wherein the conducting member is disposable.

16. The method of claim 11, wherein the conductive fibers are present in an amount ranging from about 1 wt. % to about 90 wt. %, based on the total weight of the nonwoven material.

17. The method of claim 11, wherein the conductive fibers comprise carbon, copper, aluminum, silver, or a combination thereof.

18. The method of claim 11, wherein the nonwoven material further comprises cellulosic fibers.

19. The method of claim 11, wherein the method reduces the amount of microorganisms on the surface by at least about 1 log (90%).

20. The method of claim 11, wherein the method reduces the amount of microorganisms on the surface by about 2 log (99%).

* * * * *